United States Patent
Mozes et al.

(10) Patent No.: US 11,259,894 B2
(45) Date of Patent: Mar. 1, 2022

(54) TRACKING AND GUIDANCE ARRANGEMENT FOR A SURGICAL ROBOT SYSTEM AND RELATED METHOD

(71) Applicant: NEOCIS INC., Miami, FL (US)

(72) Inventors: Alon Mozes, Miami Beach, FL (US); Sarvagya Vaish, Coral Gables, FL (US); David Peter Cole, Bay Harbor Islands, FL (US); Ryan Anderson, Aventura, FL (US); Wuwei He, Miami Beach, FL (US); Juan Salcedo, Coral Gables, FL (US); William Chu-Hyon McMahan, Cambridge, MA (US)

(73) Assignee: Neocis, Inc., Miami Beach, FL (US)

( * ) Notice: Subject to any disclaimer, the term of this patent is extended or adjusted under 35 U.S.C. 154(b) by 7 days.

(21) Appl. No.: 15/269,449

(22) Filed: Sep. 19, 2016

(65) Prior Publication Data

US 2018/0078332 A1    Mar. 22, 2018

(51) Int. Cl.
*A61C 1/00*    (2006.01)
*A61B 90/50*    (2016.01)
(Continued)

(52) U.S. Cl.
CPC ............ *A61C 1/0015* (2013.01); *A61B 34/20* (2016.02); *A61B 34/30* (2016.02); *A61B 90/50* (2016.02);
(Continued)

(58) Field of Classification Search
CPC ..... A61C 1/0015; A61C 1/145; A61C 1/0007; A61C 1/082; A61C 1/084; A61C 3/02;
(Continued)

(56) References Cited

U.S. PATENT DOCUMENTS

| 7,024,237 B1* | 4/2006 | Bova | ................... | A61N 5/1049 |
| | | | | 600/429 |
| 8,938,282 B2* | 1/2015 | Daon | ..................... | A61B 6/145 |
| | | | | 600/424 |

(Continued)

FOREIGN PATENT DOCUMENTS

| CN | 1115630 | 1/1996 |
| CN | 1728970 | 2/2006 |

(Continued)

*Primary Examiner* — Edward Moran
(74) *Attorney, Agent, or Firm* — Womble Bond Dickinson (US) LLP

(57) ABSTRACT

A tracking and guidance arrangement for a surgical robot system and related method are provided. The arrangement includes a patient-interacting device including an instrument engaged a distal end of a guide arm and a fiducial marker coupled to maxillofacial anatomy of the patient. A detector is connected to an articulating arm and co-operable therewith to be positioned adjacent to the fiducial marker, with the detector being configured to interact with the fiducial marker. A controller device is configured to receive data from the detector relative to the interaction thereof with the fiducial marker, to determine a spatial relation between the fiducial marker and the detector based on the data, to determine a spatial relation of the instrument relative to the fiducial marker, and to direct the instrument to interact with the maxillofacial anatomy of the patient according to the determined spatial relations.

18 Claims, 3 Drawing Sheets

Figure 1:
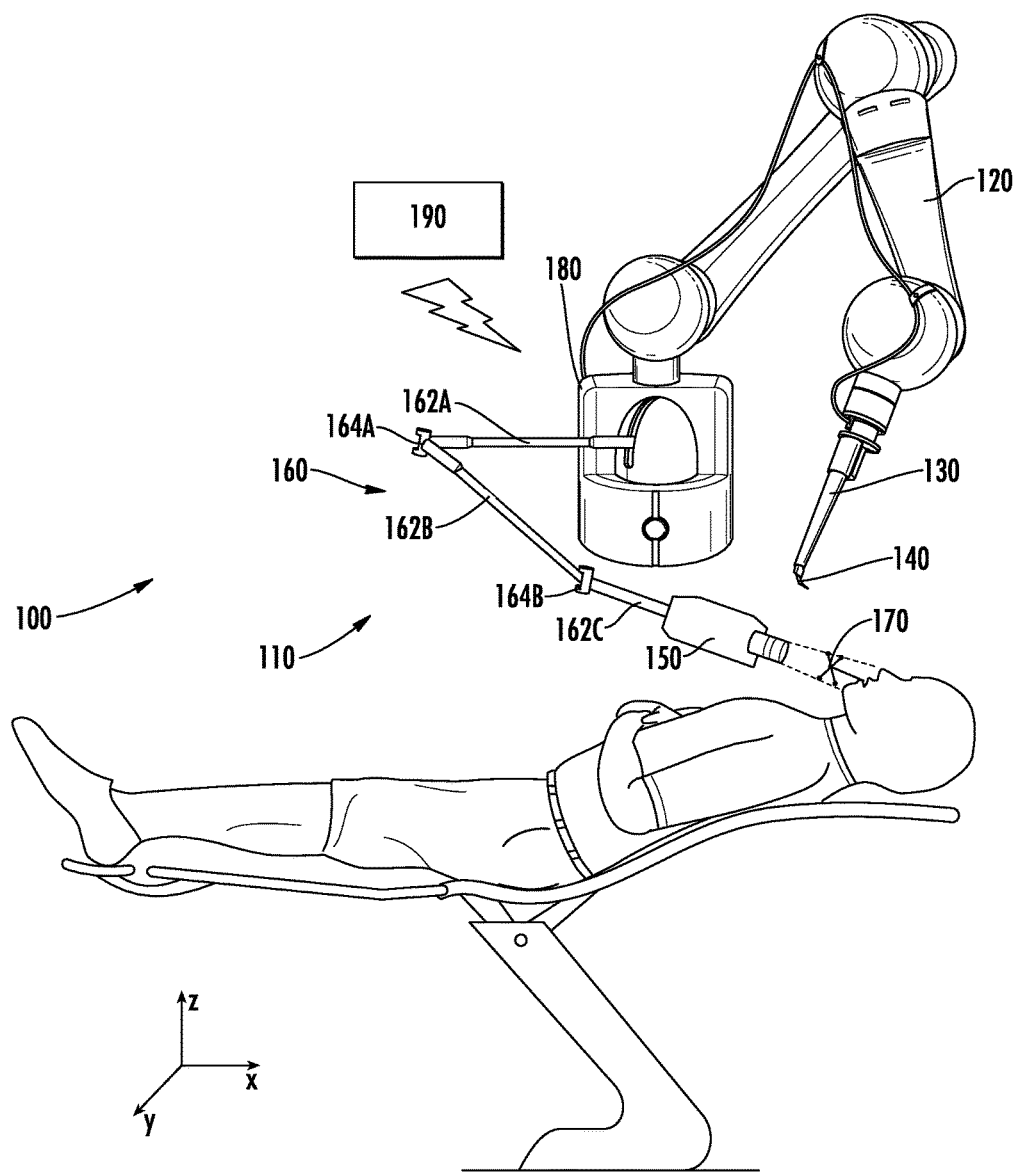

(51) Int. Cl.
*A61C 1/08* (2006.01)
*A61B 34/20* (2016.01)
*A61B 34/30* (2016.01)
*A61C 1/14* (2006.01)
*A61C 3/02* (2006.01)

(52) U.S. Cl.
CPC ............. *A61C 1/00* (2013.01); *A61C 1/084* (2013.01); *A61C 1/145* (2013.01); *A61C 3/02* (2013.01); *A61B 2034/2051* (2016.02); *A61B 2034/2055* (2016.02); *A61B 2034/2057* (2016.02); *A61B 2034/2059* (2016.02); *A61B 2034/2063* (2016.02); *A61B 2034/2072* (2016.02)

(58) Field of Classification Search
CPC .............. A61C 8/00; A61B 2034/2051; A61B 2034/2055; A61B 2034/2063; A61B 34/00–77
USPC ........................................................... 433/75
See application file for complete search history.

(56) References Cited

U.S. PATENT DOCUMENTS

| | | | | |
|---|---|---|---|---|
| 2006/0142657 A1* | 6/2006 | Quaid | ................... | A61N 1/372 600/424 |
| 2007/0003014 A1 | 1/2007 | Boese et al. | | |
| 2007/0265495 A1* | 11/2007 | Vayser | ................... | A61B 1/045 600/109 |
| 2009/0240378 A1* | 9/2009 | Yao | ....................... | G06Q 10/06 700/291 |
| 2009/0245600 A1* | 10/2009 | Hoffman | ............ | A61B 1/00039 382/128 |
| 2009/0253095 A1* | 10/2009 | Salcedo | ................... | A61B 1/24 433/75 |
| 2013/0261433 A1* | 10/2013 | Daon | ....................... | A61C 1/00 600/424 |
| 2014/0188132 A1* | 7/2014 | Kang | ................... | A61B 6/4441 606/130 |
| 2014/0199650 A1* | 7/2014 | Moffson | ................ | A61C 1/082 433/27 |
| 2014/0272789 A1* | 9/2014 | Mozes | ................. | A61C 8/0092 433/173 |
| 2014/0276943 A1* | 9/2014 | Bowling | ................ | A61B 17/16 606/130 |
| 2014/0309523 A1* | 10/2014 | Daon | ..................... | A61B 19/50 600/424 |
| 2014/0350571 A1 | 11/2014 | Maillet et al. | | |
| 2015/0032164 A1* | 1/2015 | Crawford | ............ | A61B 19/2203 606/279 |
| 2015/0057675 A1* | 2/2015 | Akeel | ..................... | G16H 50/50 606/130 |
| 2016/0074129 A1* | 3/2016 | Merritt | ................... | A61B 90/39 433/29 |
| 2016/0157815 A1* | 6/2016 | Slak | ..................... | A61B 8/0841 433/29 |
| 2016/0354169 A1* | 12/2016 | Suttin | ..................... | A61B 34/30 |

FOREIGN PATENT DOCUMENTS

| | | |
|---|---|---|
| WO | WO 02/096261 | 12/2002 |
| WO | WO 2016/118737 | 7/2016 |

* cited by examiner

TRACKING AND GUIDANCE ARRANGEMENT FOR A SURGICAL ROBOT SYSTEM AND RELATED METHOD

BACKGROUND

Field of the Disclosure

The present application relates to surgical robots and associated guidance systems and, more particularly, to a tracking and guidance arrangement for a surgical robot system used, for example, in dental surgery, wherein the arrangement is configured to track patient movement during the surgical procedure in order to guide a surgical instrument.

Description of Related Art

Many surgical robot systems for procedures such as dental surgery procedures utilize guidance systems comprising a robotic arm to guide a surgical instrument (e.g., a drill) and a mechanical tracking arm coupled to a patient to track patient motion relative to the surgical instrument. In these systems, the robotic arm and the mechanical tracking arm are physically coupled together and calibrated so their relative positions are known. To track patient movement, the mechanical tracking arm may be either physically attached or otherwise tethered to the patient via a splint or other attachment device connected to the patient. In other instances, patient movement may be remotely tracked using, for example, optical, electromagnetic, acoustic, etc., tracking devices. In these surgical robot systems, the splint or other attachment device connected to the patient acts as a fiducial marker for reference to the movement of the patient.

However, a mechanical tracking arm that is physically attached or otherwise tethered to a patient may disadvantageously create a weight on the patient and physically constrain patient motion. This may lead to patient discomfort during the procedure. Likewise, a remote tracking device for tracking patient movement through interaction with a fiducial marker has its own disadvantages. For example, a remote optical tracking system using a stereoscopic camera requires line-of-sight to one or more fiducial markers in a large field of view, which may lead to constant repositioning of the surgical instruments, equipment, and the like, or else the line of communication (i.e., sight in the case of an optical tracking system) may otherwise be impeded during the procedure. In another example, an electromagnetic tracking system may equally be disadvantageous as interference or interruption of communication may occur, which may inhibit or prevent system efficiency.

As such, it may be desirable to provide a tracking and guidance arrangement for a surgical robot system and associated method that address and overcome these noted exemplary limitations of prior art systems. Such capabilities may desirably facilitate a more comfortable surgical experience for the patient and improved surgical efficiency.

SUMMARY OF THE DISCLOSURE

The above and other needs are met by aspects of the present disclosure which, in one particular aspect, provides a tracking and guidance arrangement for a surgical robot system, comprising a patient-interacting device including an instrument engaged with a distal end of a guide arm. The instrument may be adapted to interact with maxillofacial anatomy of a patient. The tracking and guidance arrangement also comprises a fiducial marker coupled to the maxillofacial anatomy of the patient. The tracking and guidance arrangement also comprises a detector connected to a distal end of an articulating arm and co-operable therewith to be positioned adjacent to the fiducial marker. The detector may be configured to interact with the fiducial marker. The tracking and guidance arrangement also comprises a controller device including a hardware processor and memory. The controller device may be configured to receive data from the detector relative to the interaction thereof with the fiducial marker, to determine a spatial relation between the fiducial marker and the detector based on the data, to determine a spatial relation of the instrument relative to the fiducial marker, and to direct the instrument, via the guide arm, to interact with the maxillofacial anatomy of the patient according to the determined spatial relations.

Another aspect provides a method of tracking and guiding a surgical robot system, comprising positioning a detector connected to a distal end of an articulating arm and co-operable therewith, adjacent to a fiducial marker coupled to maxillofacial anatomy of a patient, the detector being configured to interact with the fiducial marker. The method also comprises initiating interaction between the fiducial marker and the detector with a controller device in communication with the detector, the controller device including a hardware processor and memory. The method also comprises receiving, by the controller device, data from the detector relative to the interaction thereof with the fiducial marker. The method also comprises determining, by the controller device, a spatial relation between the fiducial marker and the detector based on the received data. The method also comprises determining a spatial relation of an instrument of a patient-interacting device, the instrument being connected to a distal end of a guide arm, relative to the fiducial marker. The method also comprises directing the instrument, via the guide arm, to interact with the maxillofacial anatomy of the patient according to the determined spatial relations.

These and other features, aspects, and advantages of the present disclosure will be apparent from a reading of the following detailed description together with the accompanying drawings, which are briefly described below. The present disclosure includes any combination of two, three, four, or more features or elements set forth in this disclosure, regardless of whether such features or elements are expressly combined or otherwise recited in a specific embodiment description herein. This disclosure is intended to be read holistically such that any separable features or elements of the disclosure, in any of its aspects and embodiments, should be viewed as intended, namely to be combinable, unless the context of the disclosure clearly dictates otherwise.

It will be appreciated that the summary herein is provided merely for purposes of summarizing some example aspects so as to provide a basic understanding of the disclosure. As such, it will be appreciated that the above described example aspects are merely examples and should not be construed to narrow the scope or spirit of the disclosure in any way. It will be appreciated that the scope of the disclosure encompasses many potential aspects, some of which will be further described below, in addition to those herein summarized. Further, other aspects and advantages of such aspects disclosed herein will become apparent from the following detailed description taken in conjunction with the accompanying drawings which illustrate, by way of example, the principles of the described aspects.

BRIEF DESCRIPTION OF THE SEVERAL VIEWS OF THE DRAWING(S)

Figure 2:
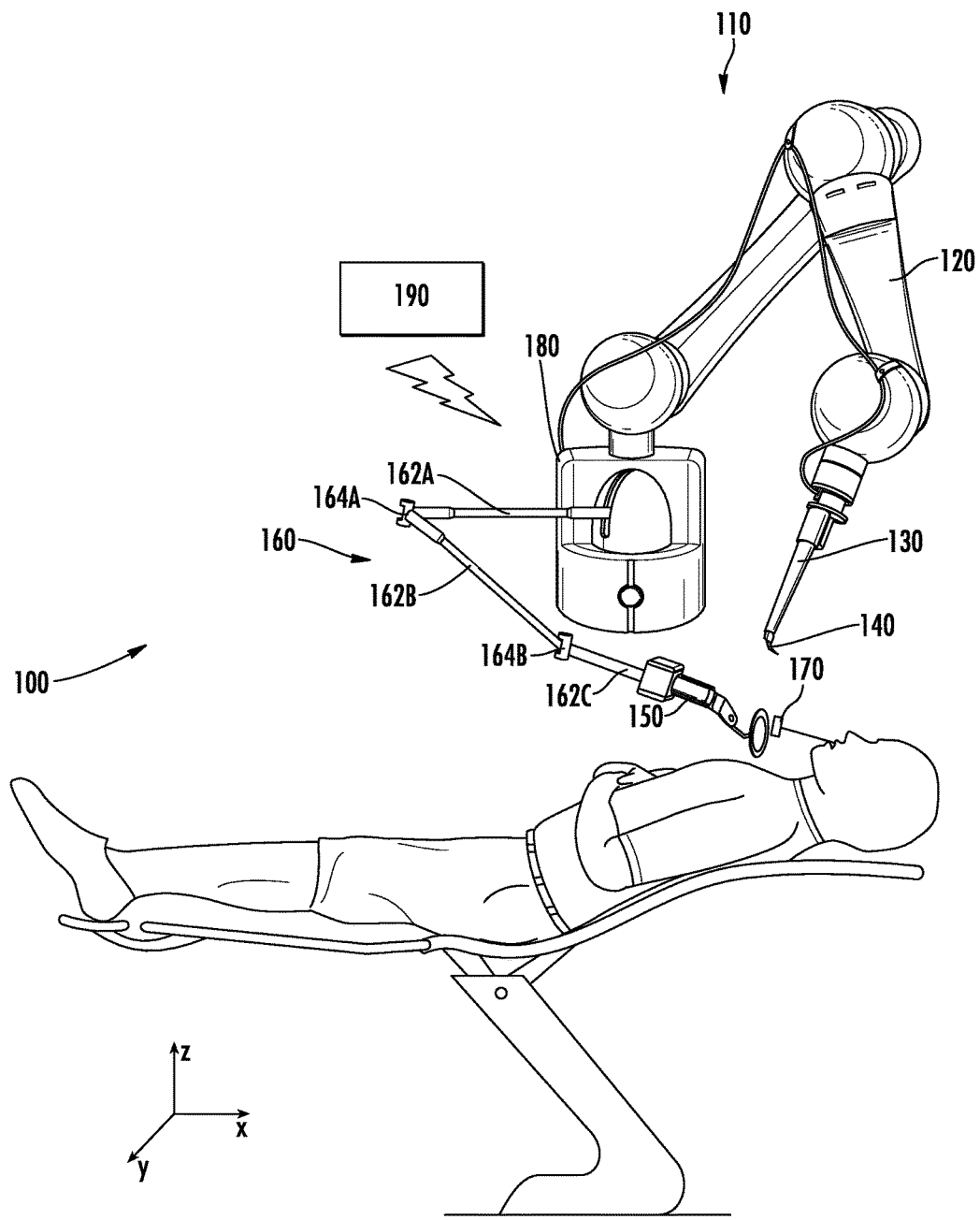
Figure 3:
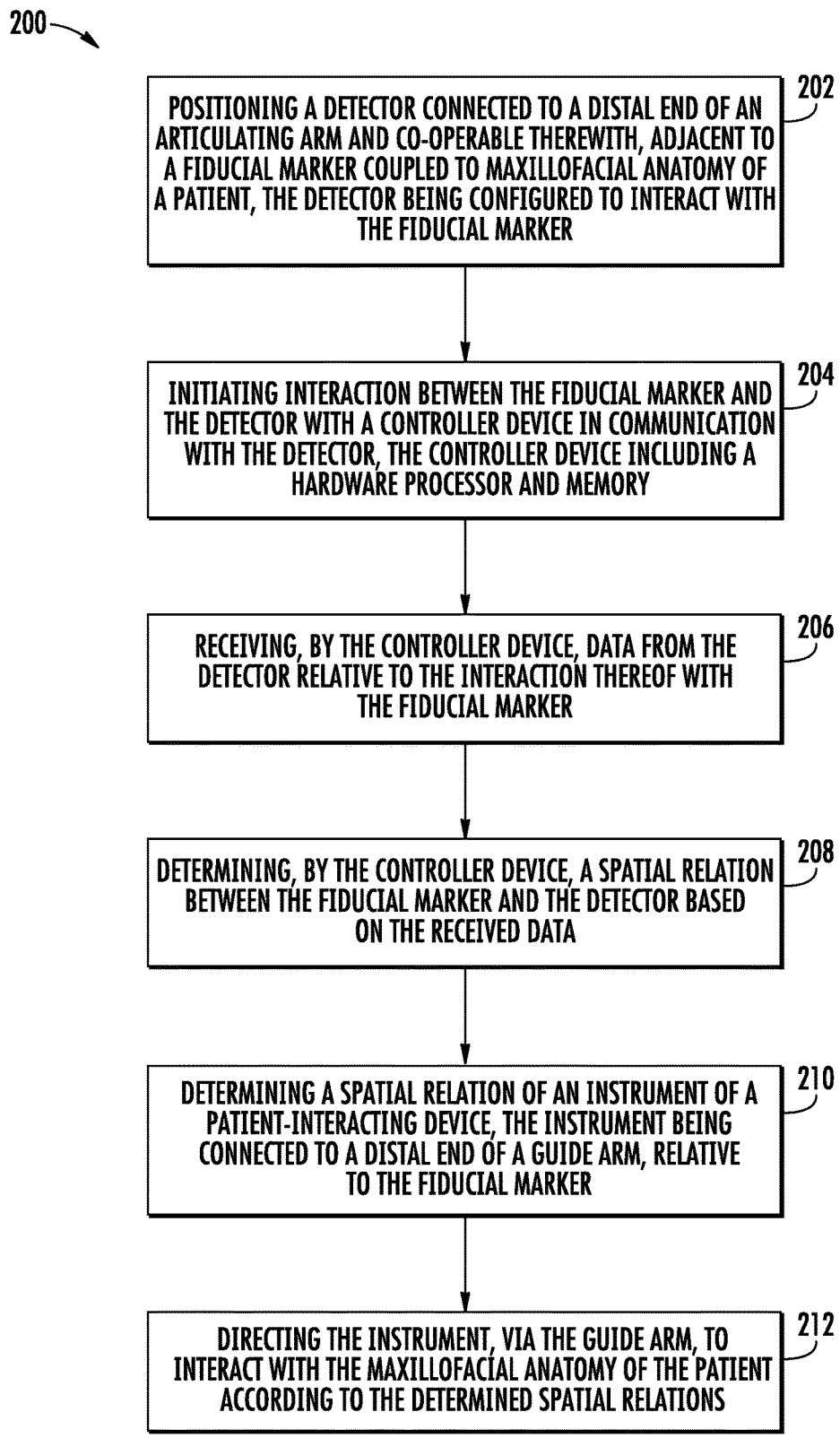

Having thus described the disclosure in general terms, reference will now be made to the accompanying drawings, which are not necessarily drawn to scale, and wherein:

FIG. 1 schematically illustrates a first exemplary embodiment of a tracking and guidance arrangement for a surgical robot system, according to various aspects of the present disclosure;

FIG. 2 schematically illustrates a second exemplary embodiment of a tracking and guidance arrangement for a surgical robot system, according to various aspects of the present disclosure; and FIG. 3 schematically illustrates a method of tracking and guiding using a tracking and guidance arrangement for a surgical robot system, according to various aspects of the present disclosure.

DETAILED DESCRIPTION OF THE DISCLOSURE

The present disclosure now will be described more fully hereinafter with reference to the accompanying drawings, in which some, but not all aspects of the disclosure are shown. Indeed, the disclosure may be embodied in many different forms and should not be construed as limited to the aspects set forth herein; rather, these aspects are provided so that this disclosure will satisfy applicable legal requirements. Like numbers refer to like elements throughout.

Various aspects of the present disclosure may be at least partially based on a guided surgical robotic system and method such as that disclosed, for example, in U.S. Pat. No. 8,808,000 to Salcedo et al. and assigned to Neocis, also the assignee of the present application. The disclosure of U.S. Pat. No. 8,808,000 to Salcedo et al. is thus incorporated by reference herein.

FIGS. 1-3 provide exemplary embodiments of tracking and guidance arrangements for surgical robot systems and associated methods. According to some aspects of the disclosure, surgical robot systems and methods may be utilized in dental applications, specifically for dental implantation procedures. However, the tracking and guidance arrangements for surgical robot systems and methods are not limited to dental applications and may be utilized for any application in which tracking movement of patient anatomy and guiding movement of a surgical implement is needed without the limitations associated with conventional surgical robot systems and methods (e.g., line-of-sight restrictions, physical tethers, interference, etc.)

Referring now to FIGS. 1-2, a surgical robot system, generally illustrated 100, is provided with respective exemplary embodiments of a tracking and guidance arrangement 110 for tracking patient motion during robotic surgery. As illustrated in FIGS. 1-2, the tracking and guidance arrangement 110 and/or the surgical robot system 100 may be configured for robotic dental surgery (e.g., dental implant surgery), although one of ordinary skill in the art will appreciate that the tracking and guidance arrangement 110 and/or the surgical robot system 100 may also be readily applicable, or otherwise readily adaptable, to other surgical procedures (e.g., skull surgery, ears, nose, and throat (ENT) surgery, orthopedic surgery, or any other surgical procedure associated with an anatomy of a patient)

With regard to FIG. 1, the tracking and guidance arrangement 110 comprises a hybrid (i.e., combined) mechanical and optical tracking and guidance arrangement, while in FIG. 2, the tracking and guidance arrangement 110 comprises a hybrid mechanical and electromagnetic tracking and guidance arrangement. In each of the illustrated exemplary tracking and guidance arrangements 110, the combination of technologies (e.g., mechanical tracking and guidance and optical tracking and guidance, or electromagnetic tracking and guidance) overcomes the noted deficiencies present in certain prior art tracking and guidance arrangements. For example, increased freedom of movement for a patient, minimized line-of-sight requirements, reduced interference potential, etc., are some exemplary improvements to the field of automated robot surgery that result from the tracking and guidance arrangement 110 according to the present disclosure. Other technology combinations for a hybrid tracking and guidance arrangement 110 are also contemplated.

Generally, and in reference to FIGS. 1-2, the tracking and guidance arrangement 110 comprises a patient interacting device 130, including a guide arm 120, such as, for example, an articulating arm member (e.g., a robotic arm), and an instrument 140 (i.e., a surgical instrument). The instrument 140 is configured to engage a distal end of the guide arm 120, and is adapted to interact or otherwise communicate with a maxillofacial anatomy (e.g., a jaw or mouth) of the patient while being guided by the guide arm 120. In some aspects, the patient-interacting device 130 may be referred to herein as a "cutting device", "drilling device", "site preparation device", "implantation device", or the like, and this reference is intended to indicate the particular instrument 140 engaged with the guide arm 120. As such, the patient-interacting device 130 and the instrument 140 may be interchangeably referred to herein as being configured for a particular corresponding purpose or procedure, with the understanding that such reference is intended to indicate that the instrument 140 element of the patient-interacting device 130 is configured to be directed or guided, via the guide arm 120, with respect to an invasive portion, or at least a patient-interacting portion of a robotic surgery procedure (e.g., to "prepare" the site within or otherwise interact with the jaw or mouth of the patient).

In some aspects, one or more actuators (not shown) may be engaged with the guide arm 120 and may be configured and arranged to cooperate to guide (i.e., translate in a particular direction (horizontal and/or vertical), and/or rotate about an axis) the distal end of the guide arm 120 in six degrees of freedom upon manipulation by the user to accomplish the surgical procedure. The guide arm 120 can also be configured to restrict or otherwise control the movement of the patient-interacting device 130, and thus the instrument 140. Further, in some instances, the guide arm 120 may have a miniature parallel structure to which the instrument 140 is secured and allowed to have full freedom of movement. Since the instrument 140 comprises or is attached to the distal portion of the guide arm 120, the patient interacting portion (i.e., the cutting/drilling tip) is the instrument 140 of the patient-interacting device 130, and the instrument 140 thus must be in a known spatial position (i.e., known to the system 100 relative to the guide arm 120).

In some aspects, the instrument 140 is guided or directed, via the guide arm 120, according to spatial relations as determined by the tracking and guidance arrangement 110. In this manner, the tracking and guidance arrangement 110 also comprises a detector 150 connected to a distal end of an articulating arm 160 and co-operable therewith, and a fiducial marker 170 coupled to the jaw or mouth of the patient. The detector 150 can comprise an optical detector (e.g., camera) or an electromagnetic detector (e.g., electromagnetic emitter) configured to interact with the fiducial marker 170, as well as other types of detectors (e.g., an acoustic detector) configured to interact with an appropriately-configured fiducial marker 170. The fiducial marker 170 may be a splint or other engaging member configured to couple to a maxillofacial anatomy (e.g., jaw, mouth) of the patient. That is, in one instance, the fiducial marker 170 is configured to engage the patient's mouth or jaw in a "firm" or secure interaction (e.g., a splint is engaged with the patient's teeth and does not move with respect to the patient's mouth). In this instance, since the splint does not move with respect to the patient's mouth, an initial spatial position of the splint in a relative coordinate system or three-dimensional space (i.e., an X, Y, Z system) may be determined. Thus, the splint can be configured to provide a fiducial marker (i.e., a known origin or coordinate element formed by the secure interaction with or otherwise associated with or attached to the splint), which can be used, for instance, to guide the instrument 140 of the patient-interacting device 130, via the guide arm 120, during the robotic surgery.

In some aspects, the interacting portion/instrument 140 of the patient-interacting device 130 may be registered or calibrated with respect to the fiducial marker 170. For example, a calibration element (not shown) may be engaged with the patient-interacting device 130 via a kinematic coupling (i.e., rigidly mounted thereto in a known, repeatable manner). One skilled in the art will thus appreciate that the interacting portion/instrument 140 of the patient-interacting device 130 can then be calibrated with various tip calibrating methods (e.g., invariant point, etc.). Once registered, the calibration element may be replaced with a cutting/drilling element (instrument 140) in the patient-interacting device 130, in a known and repeatable manner, so that calibration parameters (i.e., a position of a distal-most point and axis associated with the interacting portion/instrument 140) are maintained as registered.

In one aspect, the fiducial marker 170 is configured to be "universally applicable" (i.e., capable of forming the secure engagement with anatomy of any patient), or at least applicable across a particular range of patients (i.e., one size fits a certain size or age of patient). In order to determine a reference origin associated with the fiducial marker 170, according to one aspect of the disclosure, the fiducial marker 170 (e.g., a splint or other engaging member) may be engaged with the patient's teeth, and the patient's jawbone structure then imaged using, for example, computerized tomography (CT) or any other suitable imaging technique such as, for instance, magnetic resonance imaging (MRI). In such instances, the fiducial marker 170 may be comprised of, for example, a radiopaque material that can be clearly defined in the image obtained, e.g., by CT or MRI, such that the fiducial marker 170 is readily identifiable, or is otherwise detectable, in images of the patient's jawbone structure. The fiducial marker 170 can thus be established, for instance, as a reference origin of a relative coordinate system or three-dimensional space.

One skilled in the art will appreciate that the fiducial marker 170 may be configured in many different manners to accomplish the desired function as discussed herein. In one aspect, the fiducial marker 170 may be configured based on a type of detector 150 implemented in the tracking and guidance arrangement 110. Where the detector 150 is an optical detector, for example, the fiducial marker 170 may comprise reflective markers (i.e., a geometry or other characteristic or feature that uniquely defines the fiducial marker 170 in a three-dimensional space such that the fiducial marker is readily identified in images of the patient's jawbone structure, or is otherwise detectable and trackable) for the optical detector 150 to track or otherwise interact (see, e.g., FIG. 1). In another example, where the detector 150 is an electromagnetic detector, the fiducial marker 170 may comprise an appropriate sensor or emitter for the electromagnetic detector 150 to track or otherwise interact with (see, e.g., FIG. 2).

In another aspect, the fiducial marker 170 may be configured to couple to the maxillofacial anatomy of the patient in an appropriate manner based on a condition of the patient. For example, the fiducial marker 170 may be rigidly attached to the patient's mouth if the patient has some strong teeth capable of supporting the fiducial marker using, e.g., an adhesive or with a suitable clamp. In another example, for edentulous patients (i.e., those without teeth), bone pins may be drilled through the fiducial marker 170 and into the patient's jawbone structure to fasten the fiducial marker 170 securely into place. The fiducial marker 170 may also be attached to the jawbone structure of any patient using, for example, appropriate bone screws. In a further aspect, the positioning of the fiducial marker with respect to the patient's mouth may not be critical or important, as long as the fiducial marker 170 remains rigidly in place.

Accordingly, in some aspects of the present disclosure, the detector 150 may be configured to or be capable of being positioned adjacent to the fiducial marker 170, via the articulating arm 160, in order to track movement of the patient by near proximity interaction with the fiducial marker 170. Notably, the tracking and guidance arrangement 110 illustrated in FIGS. 1-2 is not configured such that the detector 150 and the fiducial marker 170 are physically connected. Rather, the articulating arm 160 is advantageously configured to position the detector 150 adjacent or near the fiducial marker 170. For example, the articulating arm 160 is configured to position the detector 150 within several centimeters of the fiducial marker 170. In this manner, a patient is not physically tethered to the surgical robot system, and the detector 150 may be positioned in a range suitable to interact with the fiducial marker 170, without some of the limitations encountered in the prior art such as, for example, impedance of communication (i.e., interruption of the line of sight in the case of an optical detector), interference, or distance of the detector from the fiducial marker.

The articulating arm 160 may comprise a plurality of serially-disposed sections 162A-C, with adjacent sections 162A-C being connected by a joint 164A-B. The joints 164A-B may be kinematic mechanisms that enable each of the serially-disposed sections 162A-C to be independently positionable (i.e., translatable, movable, rotatable) within the relative coordinate system or three-dimensional space. In each of FIGS. 1-2, three serially disposed sections 162A-C are illustrated with a first section 162A having a proximal end mounted to a base 180, a second section 162B connected at a proximal end to a distal end of the first section 162A by a first joint 164A, and a third section 162C connected at a proximal end to a distal end of the second section 162B by a second joint 164B. The detector 150 is connected to a distal end of the third section 162C using, for instance, a mechanical linkage. For example, an additional joint similar to joints 164A-B may be disposed at the distal end of the third section 162C and/or at the proximal end of the first section 162A at which the articulating arm 160 is mounted or otherwise coupled to the base 180. Otherwise, the detector 150 may be rigidly connected to the distal end of the third section 162C. In this manner, manipulation of one or more of the serially-disposed sections 162A-C of the articulating arm 160 may enable the detector 150 to pivot, move, and/or otherwise be positioned in a desired position relative to the fiducial marker 170. As one of ordinary skill in the art will note, a number of serially disposed sections and/or joints more or less than the number illustrated in FIGS. 1-2 may be utilized in the articulating arm 160.

In some aspects, the articulating arm 160 is mounted to the base 180 such that the articulating arm 160 and the guide arm 120 are operably connected, coupled, or in communication via the base 180. For example, the articulating arm 160 and the guide arm 120 may be mechanically linked to one another at proximal ends, at the base 180, or at another location along a length of each of the arms. In other aspects, the articulating arm 160 may be mounted to the base 180 such that the articulating arm 160 and the guide arm 120 are disposed in a spaced-apart relation relative to one another. Regardless, the base 180 may be, advantageously, mobile for ease of use in a variety of different spaces, patient positions (e.g., supine, upright, reclined), surgical needs, etc. Otherwise, the articulating arm 160 and/or the guide arm 120 may be mounted to a non-mobile base (e.g., a stationary platform, such as a wall, ceiling, floor, etc.). Whichever the manner in which the articulating arm 160 and/or the guide arm 120 are mounted, the resulting mounting arrangement may enable the articulating arm 160 to position the detector 150 adjacent to the fiducial marker 170, and may allow the guide arm 120 of the patient-interacting device 130 to direct the instrument 140 to interact with the maxillofacial anatomy of the patient.

As FIGS. 1-2 disclose a tracking and guidance arrangement 110 where the detector 150 and the fiducial marker 170 are disposed adjacent to one another rather than coupled together, a spatial relation between the fiducial marker 170 and the detector 150 may be determined based on data (e.g., tracking data) resulting from the interaction between the fiducial marker 170 and the detector 150. In order determine the spatial relation between these two components, as well as perform other functionality associated with tracking and guidance for a robot surgical system 100, the tracking and guidance arrangement 110 may further comprise a controller device 190 including a hardware processor and memory operably engaged with one or more components of the tracking and guidance arrangement 110. As illustrated in FIGS. 1-2, for example, the controller device 190 is in wireless communication via a communication element (not shown) with at least the detector 150, the articulating arm 160, the guide arm 120, the patient-interacting device 130, and the instrument 140. In some aspects, the communication element may be a wireless transceiver, a hardwire connection, or any other suitable mechanism, whether electrical, mechanical, electromechanical, acoustic, or optical in nature.

The controller device 190 may comprise a special purpose computer device disposed either separately from or integrated with the base 180. The controller device 190 may be configured to determine a reference point or origin associated with the fiducial marker 170 in a defined relative coordinate system or three-dimensional space, to articulate the detector 150 relative to the fiducial marker 170 so that the detector 150 is disposed in a desired position adjacent to the fiducial marker 170, to determine a spatial position of the detector 150 in the defined relative coordinate system or three-dimensional space once the detector 150 is articulated into the desired position, to initiate interaction between the detector 150 and the fiducial marker 170, to receive data from the detector 150 relative to the interaction thereof with the fiducial marker 170, and to determine a spatial relation between the fiducial marker 170 and the detector 150 based on the data.

In some aspects, determining a reference point or origin associated with the fiducial marker 170 may be accomplished by imaging the fiducial marker 170 coupled to the patient while the patient is in an initial position in a defined relative coordinate system or three-dimensional space. The controller device 190 may be configured to initiate the imaging by interfacing with whatever imaging modality is utilized (e.g., CT or MRI imaging). The image(s) or data may be stored in a data storage device (not shown) associated with the controller device 190 and utilized to establish an initial position of the fiducial marker 170 within the relative coordinate system or three-dimensional space as being an origin.

In some aspects, articulating the detector 150 relative to the fiducial marker 170 so that the detector 150 is disposed in a desired position adjacent to the fiducial marker 170, may be accomplished by manipulating one or more of the serially-disposed sections 162A-C relative to the fiducial marker 170. For example, a peripheral device (e.g., a trackball or joystick in conjunction with, for example, 3D goggles, all not shown) associated with the controller device 190 may be used to assist with or otherwise permit virtual manipulation of one or more of the serially-disposed sections 162A-C of the articulating arm 160. Otherwise, an operator of the robot surgical system 100 may manually manipulate one or more of the serially-disposed sections 162A-C of the articulating arm 160 to move the detector 150 into the desired position.

In some aspects, a spatial position of the detector 150 in the defined relative coordinate system or three-dimensional space, once the detector 150 is articulated into the desired position, may be determined by the controller device 190 receiving angular relations communications from one or more position-indicating device (e.g., an encoder). More particularly, the one or more position-indicating devices (not shown) may be engaged with one or more of the joints 164A-B for indicating an angular relation between the serially-disposed sections 162A-C engaged therewith in the defined relative coordinate system or three-dimensional space. The position-indicating device and the controller device 190 may be in communication with one another such that the one or more position-indicating devices communicate to the controller device 190 the angular relations of the joints within the defined relative coordinate system or three-dimensional space. Where the detector 150 is disposed at a distal end of the third section 162C, the controller device 190 may be configured to determine the spatial position of the detector 150 based on the angular relations of each joint 164A-B communicated thereto, as well as based on other information, such as, for example, a length of each section 162A-C. Such data relating to the spatial position of the detector 150 may be stored in a data storage device associated with the controller device 190.

In some aspects, once the articulating arm 160 is in a desired position in the defined relative coordinate system or three-dimensional space, the controller device 190 may be configured to initiate interaction between the detector 150 and the fiducial marker 170. The controller device 190 may be in communication with the detector 150 and may be configured to initiate and/or actuate operation of the detector 150. For example, where the detector 150 is a camera or other image capturing device, the controller device 190 may be configured to actuate the detector 150 to acquire images of the fiducial marker 170 coupled to the patient at a specified frame rate. In such aspects, the peripheral device associated with the controller device 190 may be configured to continuously assist or otherwise permit virtual manipulation of the one or more serially disposed sections 162A-C of the articulating arm 160 so that optimal spacing (e.g., several centimeters) is maintained between the detector 150 and the fiducial 170. In other such aspects, feedback communication between the detector 150 and the controller 190 with regard to spacing between the detector 150 and the fiducial marker 170 may be configured to automatically assist or otherwise permit virtual manipulation of the one or more serially disposed sections 162A-C of the articulating arm 160 so that optimal spacing is maintained between the detector 150 and the fiducial 170.

In some aspects, the data acquired from the detector 150 may be transmitted to the controller device 190, such that the controller device receives the data from the detector 150 relative to the interaction thereof with the fiducial marker 170. The detector 150 and the controller device 190 may be in either wired or wireless communication via the communication element.

In some aspects, to determine a spatial relation between the fiducial marker 170 and the detector 150, the controller device 190 may be configured to utilize the reference point or origin associated with the fiducial marker 170 and the spatial position of the detector 150 in the desired position to determine a first spatial relation therebetween. Subsequently, the controller device 190 may be configured to utilize the images acquired from the detector 150 to track movement of the fiducial marker 170 in the defined relative coordinate system or three-dimensional space. For example, the controller device 190 may be configured to compare the data regarding the original reference point or origin associated with the fiducial marker 170 against subsequent data acquired by the detector 150 in order to determine if a spatial position of the fiducial marker 170 has changed. Using this comparison in light of the known spatial position of the detector 150, the controller device 190 may determine a changed spatial relation between the fiducial marker 170 and the detector 150. In this manner, movement of the patient may be continuously tracked by the detector 150.

In some aspects, the surgical robot system 100 or the controller device 190 may also comprise a planning device or otherwise include planning functionality for allowing a user to develop a virtual surgical plan, as otherwise disclosed herein, in conjunction with the hardware and/or software of the system 100. In some aspects, the virtual surgical plan may be created in relation, for example, to the defined relative coordinate system or three-dimensional space (relative or absolute), as will be appreciated by one skilled in the art, and configured to associate planning parameters with the fiducial marker 170 (or other reference with respect to the patient). The controller device 190 may be configured to register the patient-interacting device 130 and/or the instrument 140 with the fiducial marker 170. In some aspects, the planning parameters may define a spatial relation between the fiducial marker 170 and the patient-interacting device 130 at different portions of or continuously during the surgical procedure. However, if the patient moves, the patient-interacting device 130 may need to compensate for patient movement by returning the instrument 140 to a defined spatial relation between the patient-interacting device 130/instrument 140 and the fiducial marker 170 as defined at a specific point in the virtual surgical plan. In some aspects, an operator of the surgical robot system 100 may perform surgery without the assistance of a virtual surgical plan.

The controller device 190 may be configured and arranged to appropriately compare the determined spatial relation between the fiducial marker 170 and the detector 150 to the patient-interacting device 130 in order to determine a spatial relation of the instrument 140 relative to the fiducial marker 170. In this instance, the determined spatial relation between the fiducial marker 170 and the detector 150 may comprise a change in the position of the patient that may be relative or proportional to a change in, or otherwise affect, the spatial relation between the fiducial marker 170 and the patient-interacting device 130/instrument 140. The controller device 190 may then be configured to compensate for the change in the spatial relation between the fiducial marker 170 and the patient-interacting device 130/instrument 140 due to the movement of the patient as reflected in the change in the fiducial marker 170 detected by the detector 150. For example, the controller device may be configured to direct (i.e., adjust) or physically guide a spatial position of the patient-interacting device 130/instrument 140 to return to the planned spatial relation between the patient-interacting device 130/instrument 140 and the fiducial marker 170 as defined in the virtual surgical plan. In other instances, for example, if the deviation between the instrument 140 and the fiducial marker 170 is over a threshold, indicating excessive movement of the patient or other issue, the controller device 190 may direct that an alarm be emitted, or even that the virtual surgical plan be aborted and the instrument 140 retracted to a safe position. The guide arm 120 may otherwise be configured to direct the patient-interacting device 130/instrument 140 into the planned spatial relation between the patient-interacting device 130/instrument 140 and the fiducial marker 170 based on communications from the controller device 190. Accordingly, the controller device 190 is configured to change the spatial relation of the patient-interacting device 130/instrument 140 relative to the fiducial marker 170, in relation to a detected change in the spatial relation between the fiducial marker 170 and the detector 150, for instance, due to patient movement.

Referring now to FIG. 3, an exemplary method, generally designated 200, of tracking and guiding a surgical robot system is disclosed. The tracking and guidance arrangement may comprise a hybrid arrangement similar to that described in reference to FIGS. 1-2 (e.g., element 110). Accordingly, the following exemplary method 200 will be described herein using the reference number conventions associated with FIGS. 1-2. Notably, the tracking and guidance arrangement may comprise a hybrid of, for example, electrical, mechanical, electromechanical, acoustic, and optical mechanisms for tracking and guidance.

In a first step 202, a detector 150 connected to a distal end of an articulating arm 160 and co-operable therewith is positioned adjacent to a fiducial marker 170 coupled to maxillofacial anatomy (e.g., jaw or mouth) of a patient, the detector 150 being configured to interact with the fiducial marker 170. As illustrated in FIG. 1, the tracking and guidance arrangement 110 comprises a hybrid mechanical and optical tracking and guidance arrangement 110, where the detector 150 engaged with the articulating arm 160 comprises an optical detector (e.g., a camera) and the fiducial marker 170 comprises one or more reflective markers. By contrast, as illustrated in FIG. 2, the tracking and guidance arrangement 110 comprises a hybrid mechanical and electromagnetic tracking and guidance arrangement 110, where the detector 150 comprises an electromagnetic detector (e.g., an emitter) and the fiducial marker 170 comprises one or more sensors or emitters. Notably, the tracking and guidance arrangement 110 may also comprise a hybrid of, for example, electrical, mechanical, electromechanical, acoustic, and optical devices for tracking and guidance.

In a second step 204, an interaction between the fiducial marker 170 and the detector 150 is initiated with a controller device 190 in communication with the detector 150. In some aspects, the controller device 190 includes a hardware processor and memory.

In a third step 206, the controller device 190 receives data from the detector 150 relative to the interaction thereof with the fiducial marker 170.

In a fourth step 208, the controller device 190 determines a spatial relation between the fiducial marker 170 and the detector 150 based on the received data.

In a fifth step 210, the controller device 190 determines a spatial relation of an instrument 140 of a patient-interacting device 130, the instrument 140 being connected to a distal end of a guide arm 120, relative to the fiducial marker 170.

In a sixth step 212, the instrument 140 is directed, via the guide arm 120, to interact with the maxillofacial anatomy of the patient according to the determined spatial relations.

Many modifications and other embodiments of the inventions set forth herein will come to mind to one skilled in the art to which these disclosed embodiments pertain having the benefit of the teachings presented in the foregoing descriptions and the associated drawings. Therefore, it is to be understood that embodiments of the invention are not to be limited to the specific embodiments disclosed and that modifications and other embodiments are intended to be included within the scope of the invention. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the disclosure. In this regard, for example, different combinations of elements and/or functions than those explicitly described above are also contemplated within the scope of the disclosure. Although specific terms are employed herein, they are used in a generic and descriptive sense only and not for purposes of limitation.

It should be understood that although the terms first, second, etc. may be used herein to describe various steps or calculations, these steps or calculations should not be limited by these terms. These terms are only used to distinguish one operation or calculation from another. For example, a first calculation may be termed a second calculation, and, similarly, a second step may be termed a first step, without departing from the scope of this disclosure. As used herein, the term "and/or" and the "/" symbol includes any and all combinations of one or more of the associated listed items.

As used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

That which is claimed:

1. A tracking and guidance arrangement for a surgical robot system, the system comprising:
    a patient-interacting device including an instrument engaged with a distal end of a guide arm, the instrument being adapted to interact with maxillofacial anatomy of a patient;
    a fiducial marker adapted to be coupled to the maxillofacial anatomy of the patient;
    a single detector connected to a distal end of a single articulating arm and co-operable therewith to be positioned adjacent to and in an uncoupled, spaced-apart relation in a three-dimensional coordinate space with the fiducial marker, the single detector connected to the distal end of the single articulating arm and comprising a single camera or a single electromagnetic detector, and the single detector being arranged to interact with and to detect the fiducial marker; and
    a controller device including a hardware processor and memory, the controller device being in communication with the single detector, the guide arm, and the articulating arm and being configured to:
        receive data from the single detector regarding the detection of the fiducial marker,
        determine an actual spaced-apart relation in the three-dimensional coordinate space between the fiducial marker and the single detector based on the data,
        compare the actual spaced-apart relation to a predetermined spaced-apart relation in the three-dimensional coordinate space between the single detector and the fiducial marker,
        manipulate the single detector or the articulating arm to move the single detector in three dimensions to the actual spaced-apart relation equal to the predetermined spaced-apart relation in the three-dimensional coordinate space between the single detector and the fiducial marker,
        determine a spatial relation in the three-dimensional coordinate space between the instrument and the fiducial marker relative to a spatial relation in the three-dimensional coordinate space between the single detector, the articulating arm, and the guide arm, and
        direct the instrument, via the guide arm, to interact with the maxillofacial anatomy of the patient according to the determined spatial relation in the three-dimensional coordinate space between the instrument and the fiducial marker.

2. The arrangement according to claim 1, wherein the guide arm is disposed in spaced-apart relation to the articulating arm.

3. The arrangement according to claim 1, wherein the articulating arm is connected to the guide arm.

4. The arrangement according to claim 1, wherein a proximal end of each of the guide arm and the articulating arm is mounted to a common base.

5. The arrangement according to claim 1, wherein the articulating arm comprises a plurality of serially-disposed sections, with adjacent sections being connected by a joint, and wherein a position indicating device in communication with the controller device is engaged with one or more of the joints for indicating an angular relation in the three-dimensional coordinate space between the serially-disposed sections engaged therewith.

6. The arrangement according to claim 5, wherein the controller device is configured to determine an actual spatial position in the three-dimensional coordinate space of the single detector engaged with the distal end of the articulating arm via the angular relations communicated by the position indicating device.

7. The arrangement according to claim 1, wherein the controller device is configured to change the spatial relation between the instrument and the fiducial marker, relative to a detected change in the actual spaced-apart relation between the fiducial marker and the single detector.

8. The arrangement according to claim 1, wherein the fiducial marker is adapted to be directly attached to the maxillofacial anatomy of the patient or engaged with a splint adapted to be mounted to the maxillofacial anatomy of the patient.

9. A method of tracking and guiding a surgical robot system, the method comprising:
 positioning a single detector connected to a distal end of a single articulating arm, adjacent to and in an uncoupled, spaced-apart relation in a three-dimensional coordinate space with a fiducial marker adapted to be coupled to maxillofacial anatomy of a patient, the single detector connected to the distal end of the single articulating arm comprising a single camera or a single electromagnetic detector, and the single detector being arranged to interact with and to detect the fiducial marker;
 initiating interaction between the fiducial marker and the single detector with a controller device in communication with the single detector, the controller device including a hardware processor and memory, and being in communication with the single detector and the articulating arm;
 receiving, by the controller device, data from the single detector regarding the detection of the fiducial marker;
 determining, by the controller device, an actual spaced-apart relation in the three-dimensional coordinate space between the fiducial marker and the single detector based on the received data;
 comparing, by the controller device, the actual spaced-apart relation to a predetermined spaced-apart relation in the three-dimensional coordinate space between the single detector and the fiducial marker;
 manipulating the single detector or the articulating arm to move the single detector in three dimensions to the actual spaced-apart relation equal to the predetermined spaced-apart relation in the three-dimensional coordinate space between the single detector and the fiducial marker;
 determining a spatial relation in the three-dimensional coordinate space between an instrument of a patient-interacting device, the instrument being connected to a distal end of a guide arm in communication with the controller device, and the fiducial marker relative to a spatial relation in the three-dimensional coordinate space between the single detector, the articulating arm, and the guide arm; and
 directing the instrument, via the guide arm, to interact with the maxillofacial anatomy of the patient according to the determined spatial relation in the three-dimensional coordinate space between the instrument and the fiducial marker.

10. The method according to claim 9, further comprising disposing the guide arm in spaced-apart relation to the articulating arm.

11. The method according to claim 9, further comprising connecting the articulating arm to the guide arm.

12. The method according to claim 9, further comprising mounting a proximal end of each of the guide arm and the articulating arm to a common base.

13. The method according to claim 9, wherein the articulating arm comprises a plurality of serially-disposed sections, with adjacent sections being connected by a joint, and wherein the method comprises engaging a position indicating device in communication with the controller device with one or more of the joints for indicating an angular relation in the three-dimensional coordinate space between the serially-disposed sections engaged therewith.

14. The method according to claim 13, further comprising determining, by the controller device, an actual spatial position in the three-dimensional coordinate space of the single detector engaged with the distal end of the articulating arm via the angular relations communicated by the position indicating device.

15. The method according to claim 9, further comprising changing, by the controller device, the spatial relation between the instrument and the fiducial marker, relative to a detected change in the actual spaced-apart relation between the fiducial marker and the single detector.

16. The method according to claim 9, comprising directly attaching the fiducial marker to the maxillofacial anatomy of the patient or engaging the fiducial marker with a splint mounted to the maxillofacial anatomy of the patient.

17. The arrangement according to claim 1, wherein the fiducial marker is an emitter, and the single detector is configured to detect the emitter.

18. The method according to claim 9, wherein the fiducial marker is an emitter, and wherein initiating interaction between the fiducial marker and the single detector comprises initiating detection of the emitter, by the single detector.

* * * * *